United States Patent

Giller et al.

[11] 3,954,760
[45] May 4, 1976

[54] PROCESS FOR PRODUCING N₁-(α-BUTYROLACTONE- AND N₁(α-VALEROLACTONE)-5-SUBSTITUTED URACILS

[76] Inventors: Solomon Aronovich Giller, ulitsa Pernavas, 10, kv. 76; Regina Abramovna Zhuk, ulitsa Gorkogo, 77, kv. 20; Anna Eduardovna Berzinya, ulitsa Raunas, 35/2, kv. 29, all of Riga, U.S.S.R.

[22] Filed: July 16, 1973

[21] Appl. No.: 379,731

[52] U.S. Cl. .................................. 260/260; 424/251
[51] Int. Cl.² ...................................... C07D 239/54
[58] Field of Search ................................... 260/260

[56] References Cited
UNITED STATES PATENTS
3,635,946  1/1972  Giller et al. ................... 260/211.5 R OTHER PUBLICATIONS
Hiller et al., *Analogs of Pyrimidines Nucleosides*, Chemistry of Heterocyclic Compounds, Vol. 4, No. 3, May–June 1968, pp. 412–413.

*Primary Examiner*—Paul M. Coughlan, Jr.
*Attorney, Agent, or Firm*—Haseltine, Lake & Waters

[57] ABSTRACT

A process for producing N₁-(α-butyrolactone)- and N₁-(α-valerolactone)-5-substituted uracils of the formula:

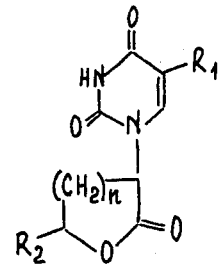

wherein $R_1$ is hydrogen, methyl, a trihalomethyl or a halogen; $R_2$ is hydrogen or an alkyl, $n = 1$ or 2, characterized in that a bis(trimethylsilyl)-5-substituted uracil of the formula:

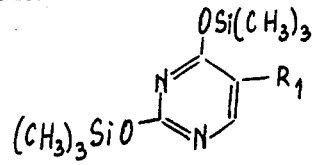

wherein $R_1$ is hydrogen, methyl, a trihalomethyl or a halogen, is treated with an α-bromolactone of the formula:

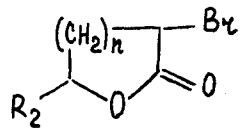

wherein $R_2$ is hydrogen or an alkyl, $n = 1$ or 2. The reaction is conducted at a temperature ranging from 80° to 160°C. From the reaction mixture thus obtained there is distilled off the resulting trimethylbromosilane formed during the reaction, and the reaction mixture is treated with a lower aliphatic alcohol.

3 Claims, No Drawings

PROCESS FOR PRODUCING N₁-(α-BUTYROLACTONE- AND N₁(α-VALEROLACTONE)-5-SUBSTITUTED URACILS

The present invention relates to processes for producing $N_1$-($\alpha$-butyrolactone)- and $N_1$-($\alpha$-valerolactone)-5-substituted uracils of the formula:

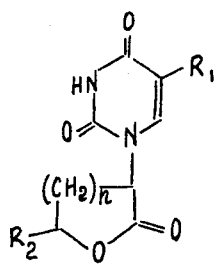

wherein $R_1$ is hydrogen, methyl, a trihalomethyl or a halogen, $R_2$ is hydrogen or an alkyl; $n = 1$ or 2.

Said compounds may be useful as such or may be employed for the production of other more complicated nucleoside analogues. Moreover, said compounds possess a pronounced bactericidal and antileucotic activity.

Known in the art is a process for the production of $N_1$-($\alpha$-butyrolactone)-5-substituted uracils, i.e. compounds corresponding to the above formula, wherein $R_1$ is hydrogen, methyl or a halogen, $R_2$ is hydrogen, $n = 1$, by alkylation of 5-substituted uracil sodium derivatives with $\alpha$-bromobutyrolactone (S. A. Giller, R. A. Thuk, Y. G. Nashatyr, journal "Chemistry of Heterocyclic Compounds", 1968, 557).

This prior art process has a disadvantage residing in a low yield of the desired products not exceeding 30%. Furthermore, the starting sodium derivatives of uracil are technologically difficult to produce.

It is an object of the present invention to provide a novel process enabling the use of more available starting components and an increase in the yield of the desired products.

This object is accomplished by a process for producing $N_1$-($\alpha$-butyrolactone)- and $N_1$-($\alpha$-valerolactone)-5-substituted uracils of the formula:

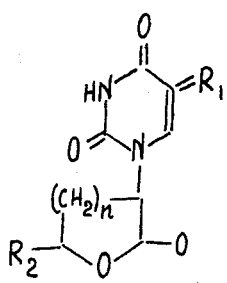

wherein $R_1$ is hydrogen, methyl, a trihalomethyl or a halogen, $R_2$ is hydrogen, an alkyl, $n = 1$ or 2, which process, according to the present invention, comprises treating a bis(trimethylsilyl)-5-substituted uracil of the formula:

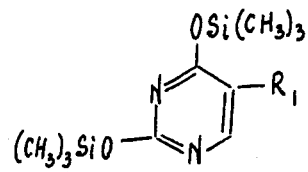

wherein $R_1$ is hydrogen, methyl, a trihalomethyl, or a halogen with an $\alpha$-bromolactone of the formula:

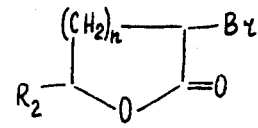

wherein $R_2$ is hydrogen or an alkyl, $n = 1$ or 2, at a temperature ranging from 80° to 160°C; the resulting trimethylbromosilane is distilled off, and the reaction mixture is treated with a lower aliphatic alcohol, whereby intermediate products, namely $N_1$-($\alpha$-butyrolactone)- and $N_1$-($\alpha$-valerolactone)-4-trimethylsilyloxy-5-substituted pyrimidin-2-ones are transformed into the final products.

The interaction of said components proceeds according to the following general scheme:

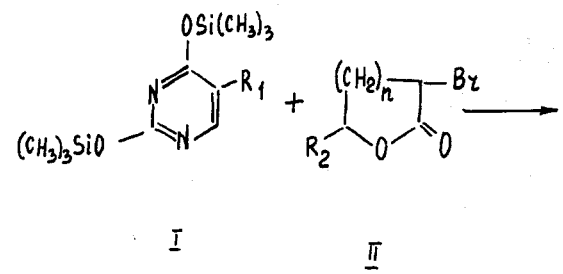

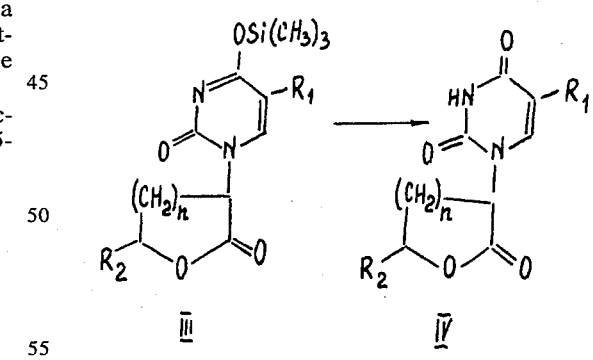

wherein $R_1$ is hydrogen, methyl, a trihalomethyl, or a halogen, $R_2$ is hydrogen or an alkyl, $n = 1$ or 2.

As follows from the above-given scheme, the process for producing $N_1$-($\alpha$-butyrolactone)- and $N_1$-($\alpha$-valerolactone)-5-substituted uracils comprises, according to the present invention, reacting a bis(trimethylsilyl)-5-substituted uracil of formula (I) with $\alpha$-bromobutyro- or $\alpha$-bromovalerolactones of formula (II) at a temperature ranging from 80° to 160°C with distilling off the resulting trimethylbromosilane formed in the reaction, whereby there are produced intermediate compounds of formula (III), i.e. $N_1$-(α-butyrolactone)-4-trimethylsilyloxy-5-substituted pyrimidin-2(IH)-ones and $N_1$-(α-valerolactone)-4-trimethylsilyloxy-5-substituted pyrimidin-2(IH)-ones. The compounds of formula III are treated with a lower aliphatic alcohol to split off the trimethylsilyl group, whereby $N_1$-(α-butyrolactone)- and $N_1$-(α-valerolactone)-5-substituted uracil derivatives of formula IV are produced.

The process according to the present invention has an advantage residing in the use of available starting compounds simplifying the process technology and isolation of the desired products with a good yield exceeding by approximately 1.5–2 times the yield of the desired product as produced by the prior-art process.

The process for producing $N_1$-(α-butyrolactone)- and $N_1$-(α-valerolactone)-5-substituted uracils is effected in the following manner.

The starting bis(trimethylsilyl)-5-substituted uracil is added to the α-bromolactone in an amount equal to ⅔ of the total amount thereof. The reaction mixture is heated for 1 hour at 80°C, treated with the remaining ⅓ of the alkylation agent, and heated under stirring at a temperature of 150°–160°C for 30 minutes, while distilling off the volatile products resulting from the reaction. The molar ratio between said uracil derivative and the alkylation agent may vary from 1 to 3, but preferably it should be 1:2. The reaction mixture is then added with ethanol and stirred for 20 minutes. The resulting precipitate is suction-filtered and recrystallized.

For a better understanding of the present invention the following Examples illustrating the production of $N_1$-(α-butyrolactone)- and $N_1$-(α-valerolactone)-5-substituted uracils are given hereinbelow.

EXAMPLE 1

Production of $N_1$-(α-butyrolactone)-uracil 11.2 g (0.1 mol) of uracil are suspended in 50 ml of hexamethyldisilazane and heated at a temperature of 160°–180°C until the uracil is completely dissolved (3 hours). The excess of the hexamethyldisilazane is distilled off under a reduced pressure in an atmosphere of nitrogen. The flask is provided with a stirrer and Dean-Stark cap with a reflux condenser. The residue obtained after the distillation and comprising 2,4-bis(-trimethylsilyl)-uracil is treated with 22 g (12 ml, 0.134 mol) of α-bromobutyrolactone and heated for 1 hour at 80°C, whereafter it is treated with an additional 11 g (6.0 ml, 0.066 mol) of α-bromobutyrolactone, and heated for 30 minutes at a temperature of 150°–160°C. The trimethylbromosilane formed during the reaction is distilled off. The reaction mixture is cooled to 40°C, treated with 20 ml of ethanol, and stirred for 20 minutes. The resulting residue is suction-filtered and recrystallized from water to give 11.8 g (60% of the theoretical amount) of $N_1$-(α-butyrolactone)-uracil melting at 238°–240°C.

pH = 2: $\lambda_{max}$ 261; ε9–800; pH = 10: $\lambda_{max}$ 264; ε7–300; 1,680; 1,710 cm$^{-1}$ ($\nu_{co}$ for uracil); 1,770 ($\nu_{C=O}$ lactone).

Found, %: C, 48.67; H, 4.18; N, 14.84. $C_8H_8N_2O_4$. Calculated, %: C, 48.98; H, 4.08; N, 14.28.

EXAMPLE 2

Production of $N_1$-(α-butyrolactone)-5-fluorouracil

The reaction is conducted as described in Example 1. Using 13 g (0.1 mol) of 5-fluorouracil, there is obtained 2,4-bis-(trimethylsilyl)-5-fluorouracil, and 33 g (18 ml, 0.2 mol) of α-bromobutyrolactone are added thereto to give 7.5 g (35% of the theoretical amount) of $N_1$-(α-butyrolactone)-5-fluorouracil in the form of a white crystalline substance, which after recrystallization from water and acetone melts at 240°–242°C.

pH = 2: $\lambda_{max}$ 268: ε8–220; pH = 10: $\lambda_{max}$ 271; ε6–200; 1,670; 1,715 cm$^{-1}$ ($\nu_{C=O}$ uracil); 1,770 cm$^{-1}$ ($\nu_{C=O}$ lactone).

Found, %: C, 44.37; H, 3.49; N, 12.70; F, 9.33. $C_8H_7N_2FO_4$. Calculated, %: C, 44.86; H, 3.29; N, 13.08; F, 8.87.

EXAMPLE 3

Production of $N_1$-γ-methyl-α-butyrolactone)-5-methyluracil

The reaction is conducted as described in Example 1. Using 12.6 g (0.1 mol) of 5-methylauracil, there is obtained 2,4-bis-(trimethylsilyl)-5-methyluracil and 35.8 g (19.5 ml, 0.2 mol) of γ-methyl-α-bromobutyrolactone are added thereto to give 13.9 g (62% of the theoretical amount) of $N_1$-(γ-methyl-α-butyrolactone)-5-methyluracil in the form of a white crystalline substance, which after recrystallization from water and acetone melts at 258°–260°C.

pH = 2: $\lambda_{max}$ 268; ε9–830; pH = 10: $\lambda_{max}$ 272; ε8–080; 1,690; 1,710 cm$^{-1}$ ($\nu_{CO}$ uracil); 1,780 cm$^{-1}$ ($\nu_{CO}$ lactone).

Found, %: C, 53.44; H, 5.38; N, 12.30. $C_{10}H_{12}N_2O_4$. Calculated, %: C, 53.57; H, 5.36; N, 12.50.

EXAMPLE 4

Production of $N_1$-(γ-methyl-α-butyrolactone)-5-trifluoromethyluracil

The reaction is conducted as described in Example 1. Using 18 g (0.1 mol) of trifluoromethyluracil, there is obtained 2,4-bis(trimethylsilyl)-5-trifluoromethyluracil and 35.8 g (19.5 ml, 0.2 mol) of γ-methyl-α-bromobutyrolactone are added thereto to give 13.3 g (48% of the theoretical amount) of $N_1$-(γ-methyl-α-butyrolactone)-5-trifluoromethyluracil in the form of a white crystalline substance which after recrystallization from water and acetone melts at 240°–242°C.

pH = 2: $\lambda_{max}$ 262; ε9–850; pH = 10: $\lambda_{max}$ 260; ε6–500. 1,670; 1,710 cm$^{-1}$ ($\nu_{CO}$ uracil); 1,770 ($\nu_{CO}$ lactone).

Found, %: C, 43.69; H, 3.33; N, 10.27; F, 20.05. $C_{10}H_9N_2O_4F_3$. Calculated, %: C, 43.17; H, 3.26; N, 10.07; F, 20.49.

EXAMPLE 5

Production of $N_1$-(α-valerolactone)-5-methyluracil

The reaction is conducted as described in Example 1. Using 12.6 g (0.1 mol) of 5-methyluracil, there is obtained 2,4-bis(trimethylsilyl)-5-methyluracil and 35.8 g (19.8 ml, 0.2 mol) of α-bromovalerolactone are added thereto to give 8.4 g (37% of the theoretical amount) of $N_1$-(α-valerolactone)-5-methyluracil in the form of a white crystalline substance melting at 260°–262°C (acetone).

pH = 2: $\lambda_{max}$ 268; $\epsilon$9–800; pH = 10: $\lambda_{max}$ 272; $\epsilon$800; 1,690; 1,710 cm$^{-1}$ ($\nu_{CO}$ uracil); 1,780 cm$^{-1}$ ($\nu_{CO}$ lactone).

Found, %: C, 53.61; H, 5.30; N, 12.32; $C_{10}H_{12}N_2O_4$. Calculated, %: C, 53.57; H, 5.36; N, 12.50.

EXAMPLE 6

Production of $N_1$-($\delta$-methyl-$\alpha$-valerolactone)-uracil

The reaction is conducted as described in Example 1. Using 11.2 g (0.1 mol) of uracil, there is obtained 2,4-bis(trimethylsilyl)-uracil and 38.6 g (20 ml, 0.2 mol) of $\delta$-methyl-$\alpha$-bromovalerolactone are added thereto to give 6.4 g (28% of the theoretical amount) of $N_1$-($\delta$-methyl-$\alpha$-valerolactone)-uracil in the form of a white crystalline substance melting at 243°–245°C (acetone).

pH = 2: $\lambda_{max}$ 261; $\epsilon$9–700; pH = 10: $\lambda_{max}$ 263; $\epsilon$7–300; 1,680; 1,710 cm$^{-1}$ ($\nu_{CO\ uracil}$; 1,770 cm$^{-1}$ ($\nu_{CO}$ lactone).

Found, %: C, 53.70; H, 5.35; N, 12.25. $C_{10}H_{12}N_2O_4$. Calculated, %: C, 53.57; H, 5.36; N, 12.50.

$N_1$-($\alpha$-butyrolactone)-5-fluorouracil is a low-toxic compound possessing an antibacterial and antileucotic activity. Its peracute toxicity on breedless white mice at a single intraperitoneal injection is 1,050 mg/kg, minimal bacteriostatic concentration on E. coli. is 3.8.10$^{-5}$ M. The compound inhibits inclusion of C$^{14}$-adenine into nucleic acids E. coli by 29% when used in a concentration of 2.5.10$^{-5}$ M.

$N_1$-($\alpha$-butyrolactone)-5-fluorouracil possesses a pronounced antileucotic action as shown by tests on three strains of interwoven leucosis of mice; generalized peracute hemocytoblastosis Le, sub-peracute lympholeucosis L 1210, and ascitic lympholeucosis Nk/Ly. The highest effect is demonstrated on a model of peracute hemocytoblastosis Le. This effect was manifested by an increase in life-span of leucotic mice which was 3 times longer then in the controls. In the case of L 1210 and Nk/Ly the life-span increase was 100 and 80% respectively. The compound reduces the leucocyte count in peripheral blood of the leucotic mice and retards or prevents development of leukemia, which is an additional indication of its efficiency.

What is claimed is:

1. A process for producing a compound of the formula:

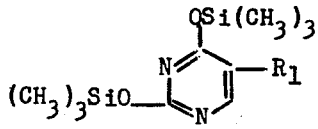

wherein $R_1$ is selected from the group consisting of hydrogen, methyl, a trihalomethyl, and a halogen; $R_2$ is selected from the group consisting of hydrogen and an alkyl; $n = 1$ to 2, consisting essentially of reacting a bis(trimethylsilyl)-5-substituted uracil of the formula:

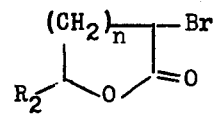

wherein $R_1$ is selected from the group consisting of hydrogen, methyl, a trihalomethyl, and a halogen, with an $\alpha$-bromolactone of the formula:

wherein $R_2$ is selected from the group consisting of hydrogen and an alkyl; $n = 1$ to 2, at a temperature ranging from 80° to 160°C; distilling off trimethylbromosilane formed in the reaction from the reaction mixture; treating the reaction mixture freed from the trimethylbromosilane with a lower aliphatic alcohol to convert the resulting $N_1$-($\alpha$-butyrolactone)-or $N_1$-($\alpha$-valerolactone)-4-trimethylsilyloxy-5-substituted pyrimidin-2(IH)-one into the compound of formula I.

2. A method according to claim 1 wherein the trihalomethyl is trifluoromethyl and the halogen is fluorine.

3. A method according to claim 2 wherein the alkyl for $R_2$ is methyl.

* * * * *